United States Patent [19]

Messina et al.

[11] Patent Number: 4,954,660

[45] Date of Patent: Sep. 4, 1990

[54] PROCESS FOR THE DIRECT HYDRATION OF LINEAR OLEFINS

[75] Inventors: Giuseppe Messina, Alghero; Carmelo Nurra, Olmedo; Oscar Cappellazzo, Alghero; Angelo Virdis, Usini; Loreno Lorenzoni, Porto Torres, all of Italy

[73] Assignee: Enichem Anic S.p.A., Palermo, Italy

[21] Appl. No.: 264,035

[22] Filed: Oct. 28, 1988

[30] Foreign Application Priority Data

Oct. 29, 1987 [IT] Italy ............................. 22450 A/87

[51] Int. Cl.$^5$ .................. C07C 27/00; C07C 29/04; C07C 41/06
[52] U.S. Cl. ......................... 568/697; 44/56; 568/896; 568/899; 568/900
[58] Field of Search ................ 568/896, 904, 694, 697

[56] References Cited

U.S. PATENT DOCUMENTS 4,320,232 3/1982 Volkamer et al. .................. 568/697
4,393,250 7/1983 Gottlieb et al. ..................... 568/697

Primary Examiner—J. E. Evans
Attorney, Agent, or Firm—Oblon, Spivak, McClelland, Maier & Neustadt

[57] ABSTRACT

Linear olefins are converted into the corresponding secondary alcohols by treatment with methyl alcohol and a tertiary alcohol, in the presence of an acidic catalyst, at a temperature ranging from 120° to 200° C. The product mixture substantially consists of the desired secondary alcohol and of the methyl ether of the charged tertiary alcohol.

The reaction products can be easily isolated by fractionation, or, in some instances, the liquid product mixture can be used as such.

Of particular interest is the direct hydration of n-butenes using tert-butyl alcohol as the tertiary alcohol. The obtained product mixture can be used as such, as an additive to methanol-containing gasolines for internal combustion engines.

11 Claims, No Drawings

PROCESS FOR THE DIRECT HYDRATION OF LINEAR OLEFINS

The present invention refers to a process for the production of secondary alcohols by the direct hydration of the corresponding linear olefins.

In particular this invention relates to a process for the production of secondary alcohols by direct hydration of the corresponding olefins which comprises reacting the olefin with a tertiary alcohol and methyl alcohol, in the presence of an acidic catalyst, at a moderately high temperature.

The process of the present invention can be applied, in line of principle, to linear olefins with any number of carbon atoms. According to a preferred embodiment of the present invention, however, said process is employed for the direct hydration of linear olefins with a number of carbon atoms higher than 3.

While, in fact, industrially exploitable alternative processes are available for the hydration of lower olefins, i.e. ethylene and propylene, no satisfactory processes are available or known in literature for the hydration of higher olefins.

According to a most preferred embodiment, the present invention is directed to a process for producing sec-butyl alcohol from the direct hydration reaction of linear butenes, because of the availability of large quantities of these last compounds as a raffinate of the methyl tert-butyl ether (MTBE) process and also because the corresponding secondary alcohol that forms (sec-butyl alcohol (SBA)), is a very important chemical product.

SBA is in fact a key intermediate in the synthesis of methyl ethyl ketone and is useful as a reactant/solvent mainly in the dye industry.

Recently, a new possible use of said product as an additive to methanol-containing hydrocarbon mixtures to be employed as fuels for internal-combustion engines has been reported, even if not fully developed.

SBA, in fact, besides improving the antiknock characteristics of these mixtures, increases the miscibility of methyl alcohol and hydrocarbons, and is devoid of any side-effect for such use.

The most commonly used method for preparing SBA, as well as other lower alkanols, is the so-called "indirect method". It involves conversion of the starting n-olefins into alkyl- and di-alkyl-sulphates by reaction with sulphuric acid, followed by hydrolysis of the thus obtained sulphates to secondary alcohols.

As far as the reaction of n-butenes is concerned (butene-1, trans butene-2, cis butene-2), very high % conversions to SBA are obtained in the overall process.

The indirect process, however, suffers from two main disadvantages: production of large quantities of undesired side-products, e.g. di-sec-butyl ether and $C_5-C_8$ hydrocarbons, and polymer formation.

Furthermore, when refiner $C_4$ streams are used as the feedstock, the presence of even small amounts of butadiene and isobutene increases the amount of polymer produced. Isobutene in the feedstock is particularly undesired because, besides homopolymerizing, it copolymerizes with the starting butenes withdrawing them from the main sulphation reaction and therefore from the subsequent formation, by hydrolysis, of the desired SBA.

Butadiene and isobutene must therefore be carefully removed from the feedstock stream in that type of process.

An additional disadvantage of the indirect process resides in the need to recycle sulphuric acid. As the concentration of the sulphuric acid issuing from the hydrolysis reactor is lower than 35%, an expensive work up step to concentrate it to the optimal concentration before recycling it, is necessary.

Third but not least disadvantageous is the corrosion of the processing equipment caused by the circulating acid.

For all the above reasons, in spite of the high conversions, the indirect process has been progressively replaced, where possible, by the "direct process". In the direct process, the hydration of the olefins to alkanols is carried out directly and in a single step, by contacting the olefin with the hydration water in the presence of an acidic catalyst. The most meaningful improvement achieved with the direct process over the indirect process, in addition to a saving in the production costs owed to the fact that the sulphation step is avoided, resides in the greater smoothness of the overall process, particularly in the work up of the reaction mixture and recovery of the reaction products.

In fact, in spite of the very low conversions, the direct process affords high selectivities in the desired products, the side-products essentially being polymerization products which, however, are present in very small amounts.

The direct hydration processes known in the art, which may be carried out in vapour-phase, liquid-phase or mixed phase, are used only for the hydration of lower olefins (ethylene and propylene) and, also in these cases, they present several problems.

The direct hydration process in vapour-phase, used for the conversion of ethylene to ethanol (US 2,579,601) and in the production of isopropanol (GB 1,269,553) involves passing of the olefins, admixed with steam, over a fixed bed of an acidic catalyst adsorbed on bentonite, celite, etc. The reaction conditions are fairly hard (T>200° C.; P=40-90 atm.); but conversions per passage are lower than 4-6%.

In this type of process, wherein conversion is controlled by the thermodynamic equilibrium (which favors the starting olefin) it is not possible to achieve higher conversions. For the same reason the process cannot be used for the hydration of olefins higher than $C_3$.

The process in liquid-phase which permits to achieve conversions remarkably higher than those afforded by the vapour-phase process, is also limited to the conversion of the lower olefins because of the low water solubility of the higher ones (butenes, pentenes, etc.).

Also the mixed phase process (water in liquid phase and olefin in vapor phase at high density) has been employed for the direct hydration of lower olefins (DE 2,147,737; DE 2,147,739; DE 2,147,740). With temperatures of about 140° C. and pressures of about 80 atm., conversions of about 75% per passage are achieved.

Among the direct hydration processes, the mixed phase process better fits the hydration of the higher olefins, mainly butenes.

The very low water solubility of butenes, however, lower the reaction yields to about 5-15% per passage (US 4,456,776; US 4,476,333), notwithstanding the more drastic reaction conditions (average T=150-170° C.). These temperatures further impair the stability of the used resins (BE 716,619) with a drop in activity higher than 15% in the first 8.000 hours of run (BE 716,619; DE 2,147,739).

Additional disadvantages of the mixed phase process are the exothermicity of the hydration process (throughout the reactor the local temperature may be few tens of degrees over the actual reaction temperature) and the high water/butene ratio (much higher than the stoichiometric value) which is needed to absorb part of the heat produced in the reaction. Both these factors affect the stability of the catalyst resin.

The direct hydration process of the present invention permits to retain high conversions of the starting linear olefins without requiring too extreme reaction conditions which would be detrimental to the activity and life of the catalyst and without involving side-reactions of the olefins themselves.

The new process of the present invention which is particularly suitable for the production of secondary alkanols with a number of carbon atoms higher than 3, by direct hydration of the corresponding linear olefins, is characterized by the fact that the water employed for the hydration is formed within the reaction environment, at the reaction conditions required for the hydration and in the presence of the acidic catalyst, from the dehydration of a tertiary alcohol.

Tertiary alcohols which can therefore be used in the process of the invention are those tertiary alcohols which easily dehydrate in the presence of an acidic catalyst and which do not negatively interfere with the reaction course. More particularly, tertiary alkanols such as tert-butyl alcohol, tert-amyl alcohol, and the like alcohols may conveniently be employed in this process.

According to a preferred embodiment of the present invention, the reaction is carried out using tert-butyl alcohol as the tertiary alcohol. Tert-butyl alcohol, in fact, has a low cost and can be easily obtained from a number of different starting compounds with known convenient methods; furthermore the methyl ether of said alcohol, which forms in the process of the invention, is a valuable component of the unleaded gasolines, acting as an octane booster.

The reaction of the present invention is actually carried out by feeding the tertiary alcohol, together with methyl alcohol and the olefin, to the hydration reactor which according to a preferred embodiment of the process of the invention, consists of a steel vertical tubular reactor packed with the supported acidic catalyst (or the acidic resin).

Without entering in detail in the reaction mechanism, the role of the starting methyl alcohol is to withdraw the unsaturated compound which forms in the dehydration of the tertiary alcohol from the thermodynamic equilibrium (by forming the corresponding methyl ether), thus avoiding its polymerization.

With reference to the hydration process of butenes with tert-butyl alcohol, which represents a preferred embodiment of the present invention, the three main reactions which occur are the following ones:

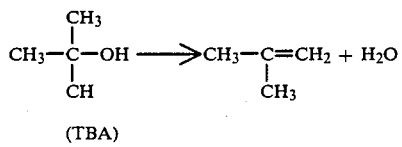
(TBA)

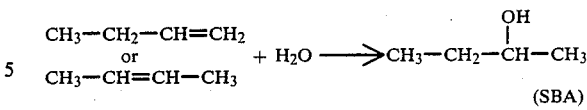

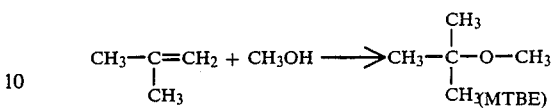

and lead to the formation of the secondary alcohol (SBA in this case) and of the methyl ether of the tertiary alcohol (MTBE in this case) starting from the tertiary alcohol (TBA), the olefin (linear butenes) and methyl alcohol.

A small amount of the methyl ether of the tertiary alcohol may also form through direct etherification of the starting tertiary alcohol by methyl alcohol. Side-products which may form in the present process are the methyl ether of the secondary alcohol, through etherification of the secondary alcohol which gradually forms with methanol, and dimethylether.

Essentially, however, the reaction products are the secondary alcohol and the methyl ether of the tertiary alcohol. Furthermore, by suitably adjusting the reaction conditions and in particular the molar ratio between the starting compounds, it is possible to reduce the amount of undesired side-products.

More particularly, a mole ratio of tertiary alcohol to starting olefin in a range of from about 0.25:1 to about 2.0:1 is conveniently employed. A molar ratio lower than 0.25:1 may also be employed but obviously the olefin % conversion per passage might thus lower to an industrially unacceptable value. Also a molar ratio higher than 2.0:1 could be employed, but the use of higher amounts of the tertiary alcohol leads to higher amounts of the unsaturated compound which form in the dehydration step, with problems in the possible recycle of the unreacted starting compounds as well as in the formation of undesired polymerization products.

Preferably, however, a mole ratio of tertiary alcohol to olefin ranging from about 0.25:1 to about 1.0:1, and more preferably from about 0.3:1 to about 0.7:1 is employed.

Methyl alcohol, the role of which, as pointed out above, is to block the unsaturated compound which forms in the dehydration of the tertiary alcohol, converting it into the corresponding methyl ether, is used in at least an equimolar amount with respect to the tertiary alcohol and preferably in an excess. Generally, a mole ratio of methyl alcohol to tertiary alcohol ranging from about 1:1 to about 5:1, and preferably from about 1.2:1 to about 3:1 is employed. Also in this case it is possible to use higher amount of methyl alcohol but excessive production of undesired side-products, such as for instance the secondary alcohol methyl ether, may occur.

As for the starting olefin, α-olefins or internal olefins, either cis or trans, can be employed as well as their mixtures in any proportion. Furthermore, and this represents an additional advantage of the process of the present invention, mixtures of linear olefins, as indicated above, containing different amounts of branched olefins, diolefins or paraffins, may also be used as the feedstock. It is therefore possible to use refinery streams with different carbon atoms, deriving from petroleum reforming processes (catalytic cracking and coking).

More particularly, for example, as for the hydration of butenes, the preferred feedstock mixture is the so-called twice-spent C$_4$ mixture containing butanes and butenes. It is also possible, however, to use C$_4$ cuts containing different amounts of isobutene, up to the maximum acceptable limit which corresponds to the amount contained in the debutadienized butenes obtained from cracking, and/or small amounts of butadiene.

In fact, while in all the processes for the direct hydration of linear olefins, branched olefins and diolefins must be carefully removed because they co-polymerize with the linear olefins withdrawing these last compounds from the hydration reaction, in the process of the invention it is not necessary to remove branched olefins and diolefins because the most favored reaction is the reaction with methyl alcohol to afford the corresponding ether.

A characteristic of the process of the present invention is that the feedstock may be free from water. It has to be pointed out, however, that while the presence of water in the feedstock is not necessary, small amounts of water are well tolerated.

In particular, the dissolved water which accompanies the reactants both in the first feed as well as in the possible recycle, or relatively higher amounts can be present.

Acidic catalysts which may be employed in the hydration process of the present invention are, for instance:

(a) strong acids supported on inert materials, e.g. sulphuric acid supported on bentonite or celite, phosphoric acid, polyphosphoric acids, sulphonic acids on silica gel, etc.
(b) ion exchange acidic resins, with a polystyrene or polystyrene crosslinked with divinylbenzene matrix, e.g. Amberlyst ® type resins (Rohm & Haas), etc.;
(c) acidic resins with a high thermal stability, e.g. polyphenylsulphonate, perfluoroepoxide and vinylsulphonic acid co-polymers (Nafion ®), etc.;
(d) heteropolyacids, either supported or not, e.g. polymerised phosphotungstates, etc.;
(e) in general terms any of those solid acidic catalysts or catalytic systems suitably employed in the direct hydration of olefins.

Optimum results have been obtained using cationic resins, and particularly sulphonated polystyrene resins optionally cross-linked with divinylbenzene.

In the practice of the process of the present invention, broad ranges of temperature and pressure conditions including those conventionally employed in the direct hydration of olefins, can be used. Usually, however, the reaction is carried out at high temperatures, typically ranging from 120 to 200° C., and, preferably, ranging from 130 to 170° C. Reaction pressures are generally in the range of from 50 to 150 atm.

The optimum temperature, within the above specified range, will substantially depend on the particular olefin which is fed and on the catalyst employed; while the optimum pressure will depend on the selected temperature, in addition to the particular olefin fed. It has to be pointed out that, as the exothermicity of the olefin hydration reaction ($\Delta H_{25°\,C} \simeq -12.1$ Kcal/mol for butene$-1$) is balanced by the endothermicity of the dehydration of the tertiary alcohol ($\Delta H_{25°\,C} \simeq +12.83$ Kcal/mol for TBA), there is a thermic equilibrium inside the reactor that allows the hydration reaction to be carried out at well defined and uniform temperature conditions.

Overheating of the catalytic bed, which is one of the disadvantages of the known processes, is thus avoided and the desired reaction products are obtained in a very high purity degree.

The direct hydration process of the present invention can be carried out in batch, contacting the reactants with the catalyst at the suitably selected temperature and pressure conditions, separating, at the end of the reaction, the reaction mixture from the catalyst and finally recovering the desired products; or it can be carried out as a continuous process, by flowing the reactants through a fixed-bed tubular reactor containing the catalyst and recovering the reaction products as they form.

The desired products can then be separated simply by fractional distillation.

When, however, according to a preferred embodiment of the present invention, the hydration process is carried out using linear butenes as the starting olefins and tert-butyl alcohol as the tertiary alcohol, at the end of the hydration process, after cooling and depressurizing, the reaction mixture will consist of two phases, a gas phase and a liquid phase, which will be easily separated. The gas phase will substantially contain the unreacted starting olefins, the possible isomerization products thereof, and the inert gas compounds possibly contained in the feedstock. The liquid phase will substantially consist of unreacted starting methyl and tert-butyl alcohols, sec-butyl alcohol, methyl tert-butyl ether, and minor amounts of mixed ethers.

While the gas phase can be recycled, with or without prior purification from certain components, the liquid phase can be employed as such, without any need of expensive fractionating steps, as an additive to methanol-containing gasolines for internal-combustion engines, with two main effects: improving the anti-knock characteristics and favoring the compatibility of methanol with the other hydrocarbon components thus avoiding any phase separation.

A further object of the present invention, is therefore the mixture of products obtained by direct hydration of linear butenes with methyl alcohol and tert-butyl alcohol according to the process of the present invention.

A further object of the present invention is the use of said mixture in the methanol-containing gasolines for internal-combustions engines.

The following examples illustrate in further detail the process of the present invention in some representative embodiments thereof and in no way they should be interpreted as a limitation to the scopes of the invention.

EXAMPLE 1

A mixture of methyl alcohol, butene-1 and tert-butyl alcohol at a 1/1/0.5 molar ratio, is passed upwardly through a tubular fixed-bed reactor (height = 30 cm; inside diameter = 1.2 cm) containing Amberlyst ® 15 (8.9 g, corresponding to a volume of 22 ml after imbibition) with a flow rate of 66 ml/h, corresponding to a residence time of 0.3 h, at 150° C. and 70 atm.

The reaction product, after cooling and depressurising, consists of:

(a) a liquid phase containing unreacted methyl alcohol and tert-butyl alcohol (TBA), sec-butyl alcohol (SBA), H$_2$O, methyl tert-butyl ether (MTBE), methyl sec-butyl ether (MSBE), di-sec-butyl ether (DSBE); and (b) a gas phase containing unreacted butene-1, isobutene, trans butene-2, cis butene-2 and dimethyl ether (DME).

The overall reaction balance is reported in following Table I

TABLE I

| Components | Feedstock | | | Product | | |
|---|---|---|---|---|---|---|
| | % w. | mol/100 g | % mol | % w. | mol/100 g | % mol |
| Methanol | 25.64 | 0.801 | 39.37 | 16.00 | 0.500 | 24.95 |
| TBA | 29.23 | 0.395 | 19.71 | 5.85 | 0.079 | 3.94 |
| SBA | | | | 7.10 | 0.096 | 4.79 |
| $H_2O$ | 0.05 | 0.003 | 0.15 | 4.78 | 0.265 | 13.22 |
| MTBE | | | | 14.43 | 0.164 | 8.18 |
| MSBE | | | | 4.40 | 0.05 | 2.50 |
| DSBE | | | | 0.40 | 0.003 | 0.15 |
| DME | | | | 1.93 | 0.042 | 2.10 |
| Butene-1 | 45.08 | 0.805 | 40.17 | 26.00 | 0.464 | 23.15 |
| Isobutene | | | | 8.50 | 0.152 | 7.58 |
| Butene-2 trans | | | | 5.24 | 0.093 | 4.64 |
| Butene-2 cis | | | | 5.37 | 0.096 | 4.79 |

Conversion of butene-1 to SBA is therefore 11.9% by mole; while conversion of butene-1 to MSBE is 6.2% by mole and conversion of butene-1 to DSBE is 0.4% by m. Productivity in sec-butyl alcohol is 4.96 mol/Kg cat./h corresponding to 2 mol of SBA per liter of catalyst after imbibition per hour.

EXAMPLE 2

A mixture of methyl alcohol, butene-1, and tert-butyl alcohol at a 1/1/0.5 molar ratio, is fed from the bottom to the top of a tubular reactor (height =30 cm; inside diameter =1.2 cm) packed with Amberlyst ® 15 (8.9 g, corresponding to a volume of 22 ml after imbibition) with a flow rate of 66 ml/h, corresponding to a residence time of 0.3 h, at 140° C. and 70 atm. The reaction mixture, after cooling and depressuring, consists of:

(a) a liquid phase containing unreacted methyl alcohol and tert-butyl alcohol, sec-butyl alcohol, $H_2O$, methyl tert-butyl ether, methyl sec-butyl ether, di-sec-butyl ether; and (b) a gas phase containing unreacted butene-1, isobutene, trans butene-2, cis butene-2 and dimethyl ether.

The global balance of the reaction is reported in following Table II

TABLE II

| Components | Feedstock | | | Product | | |
|---|---|---|---|---|---|---|
| | % w. | mol/100 g | % mol | % w. | mol/100 g | % mol |
| Methanol | 25.90 | 0.809 | 40.39 | 16.25 | 0.508 | 25.24 |
| TBA | 29.81 | 0.403 | 20.12 | 6.20 | 0.084 | 4.17 |
| SBA | | | | 4.60 | 0.062 | 3.08 |
| $H_2O$ | | | | 5.13 | 0.285 | 14.16 |
| MTBE | | | | 21.6 | 0.245 | 12.18 |
| MSBE | | | | / | / | / |
| DSBE | | | | 0.19 | 0.001 | 0.05 |
| DME | | | | 1.30 | 0.028 | 1.39 |
| Butene-1 | 44.29 | 0.791 | 39.49 | 35.55 | 0.635 | 31.56 |
| Isobutene | | | | 4.14 | 0.074 | 3.68 |
| Butene-2 trans | | | | 2.69 | 0.048 | 2.38 |
| Butene-2 cis | | | | 2.35 | 0.042 | 2.09 |

Conversion of butene-1 to SBA is therefore 7.8% by mole; while conversion of butene-1 to DSBE is 0.3% by mole.

Productivity in sec-butyl alcohol is 3.22 mol/Kg cat./h corresponding to 1.30 mol of SBA/1 of catalyst after imbibition/h.

We claim:

1. A process for preparing secbutyl alcohol and methyl t-butyl ether, which comprises:
    reacting butene-1 or butene-2 in the presence of methyl alcohol and t-butyl alcohol with an acidic catalyst selected from the group consisting of acids supported on an inert carrier, acidic resins, and heteropolyacids at a temperature of 120° to 200° C.

2. The process of claim 1 wherein the t-butyl alcohol/butene mole ratio ranges from about 0.25 to about 2.0 moles per mole of said butene.

3. The process of claim 2 wherein the t-butyl alcohol/butene mole ratio ranges from about 0.25 to about 1.0 moles per mole of said butene.

4. The process of claim 3 wherein the t-butyl alcohol/butene mole ratio ranges from about 0.3 to about 0.7 moles per mole of said butene.

5. The process of claim 1 wherein the methyl alcohol/t-butyl alcohol mole ratio ranges from about 1 to about 5 moles per mole of said t-butyl alcohol.

6. The process of claim 5 wherein the methyl alcohol/t-butyl alcohol mole ratio ranges from about 1.2 to about 3 moles per mole of said t-butyl alcohol.

7. The process of claim 1 wherein the temperature is is from 130 to 170° C.

8. The process of claim 1 wherein the acidic catalyst is selected from among the acids supported on inert carriers and the acidic resins.

9. The process of claim 8 wherein the acidic catalyst is a sulphonated resin.

10. A process for preparing sec-butyl alcohol and methyl t-butyl ether, which comprises:
    reacting butene-1 or butene-2 in the presence of from 0.25 to 2.0 moles of t-butyl alcohol per mole of starting butene and from 1 to 5 moles of methyl alcohol per mole of t-butyl alcohol with an acidic catalyst, at a temperature between 120° and 200° C. and at a pressure from 50 to 150 atm.

11. The process of claim 10, wherein, the process further comprises cooling and depressurizing the reaction system thereby obtaining a system having liquid and gas phases, and then separating the liquid phase containing the reaction products from the gas phase.

* * * * *